US005705739A

United States Patent [19]
Levine et al.

[11] Patent Number: 5,705,739
[45] Date of Patent: Jan. 6, 1998

[54] DETECTING SPECIFIC MEDICAL CONDITIONS FROM ERYTHROCYTE DENSITY DISTRUBITION IN A CENTRIFUGED ANTICOAGULATED WHOLE BLOOD SAMPLE

[76] Inventors: Robert A. Levine, 31 Pilgrim La., Guilford, Conn. 06437; Stephen C. Wardlaw, 191 N. Cove Rd., Old Saybrook, Conn. 06475

[21] Appl. No.: 703,509

[22] Filed: Aug. 27, 1996

[51] Int. Cl.⁶ .................................................. G01N 30/00
[52] U.S. Cl. ........................... 73/61.72; 436/70; 436/177; 128/760
[58] Field of Search ............................ 73/61.71, 61.41, 73/61.43, 61.72; 356/39; 436/70, 177; 128/760

[56] References Cited

U.S. PATENT DOCUMENTS

| | | | |
|---|---|---|---|
| 3,437,266 | 4/1969 | Patterson | 210/361 |
| 4,190,535 | 2/1980 | Laderer et al. | 210/83 |
| 4,558,947 | 12/1985 | Wardlaw | 356/39 |
| 4,843,869 | 7/1989 | Levine et al. | 73/61.43 |
| 5,321,975 | 6/1994 | Levine et al. | 73/61.71 |

*Primary Examiner*—Hezron E. Williams
*Assistant Examiner*—Nashmiya Ashraf
*Attorney, Agent, or Firm*—William W. Jones

[57] ABSTRACT

In most mammals studied, a histogram of the erythrocytes' density of a healthy individual normally has a Gaussian distribution. Gaussian or near-Gaussian distributions may be characterized by their mean, by their standard deviation, and their absence of skewness. A measurement of the erythrocyte density distribution (EDD) in mammalian whole blood which has been anticoagulated with heparin can yield information which is indicative of certain physiologic and pathophysiologic conditions that are characterized by various EDD abnormalities. These abnormalities may include abnormalities in the standard deviation of the EDD; the mean erythrocyte density; and any skewness of the EDD curve. The hematocrit or percent packed red cell volume, which is obtained at the same time as the EDD can also yield information. The EDD measurement is made by providing a sample of heparin anticoagulated whole mammalian blood to which is added a plurality of density markers having known individual specific gravities that are within the range of specific gravity values of mammalian erythrocytes. The blood sample-density marker mixture is centrifuged, and measurements are taken of the location of the density markers within the centrifuged erythrocyte cell pack. These measurements are analyzed to determine the standard deviation of the EDD in the sample; the mean erythrocyte density in the sample; the hematocrit value of the sample; and any skewness in the EDD curve in the sample. The resultant data is compared to empirical data obtained from patient populations with known normal and abnormal medical histories in order to determine whether there is any variation from norm of one or more of the parameters measured which are characteristic of abnormal medical conditions. Alternatively since an erythrocyte's hemoglobin concentration (HC) is the main determinant of an ethrocyte's density, HC measured on a cell counter that determines each erythrocyte's HC may be used as a surrogate for erythrocyte density. Suitable cell counters can also derive HCT from a blood sample.

5 Claims, 5 Drawing Sheets

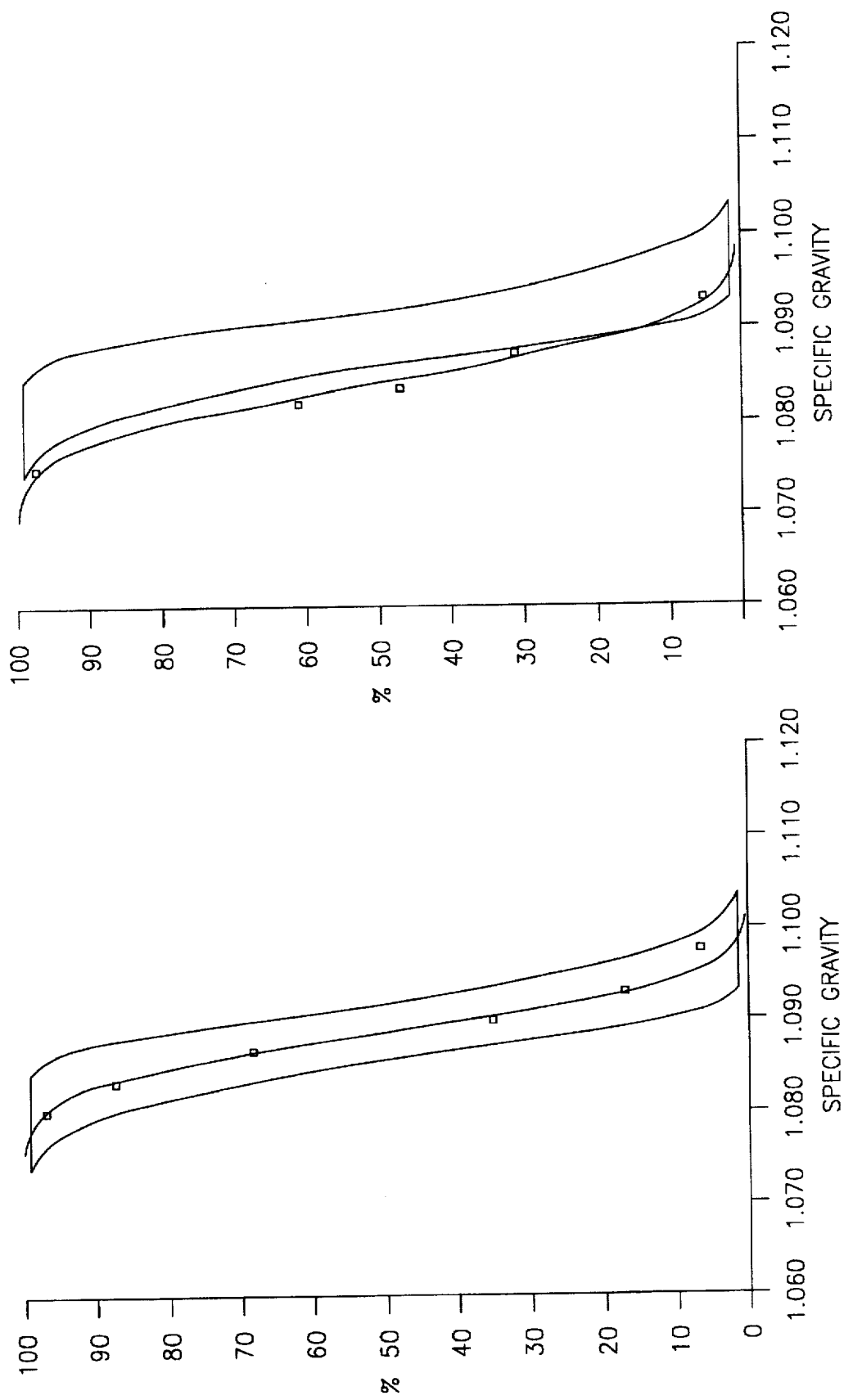

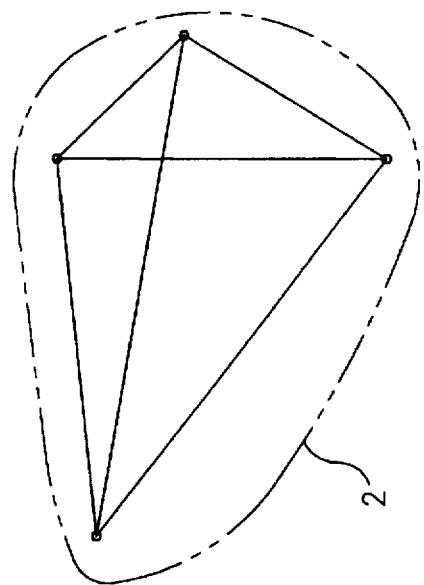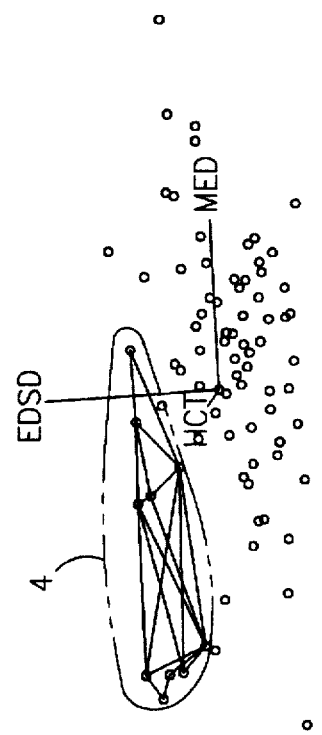
FIG. 4B
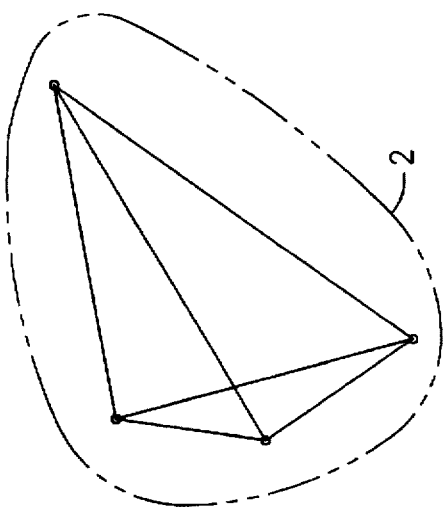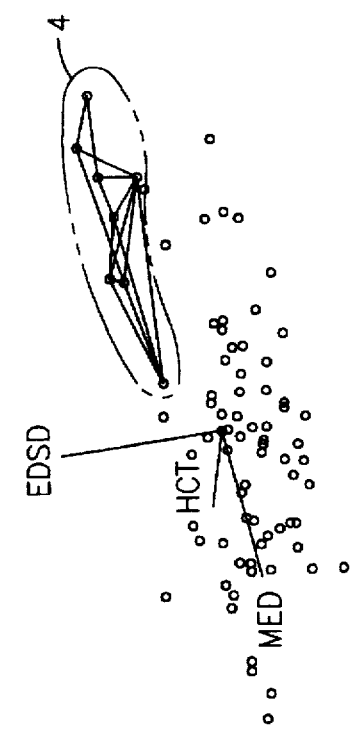
FIG. 4A

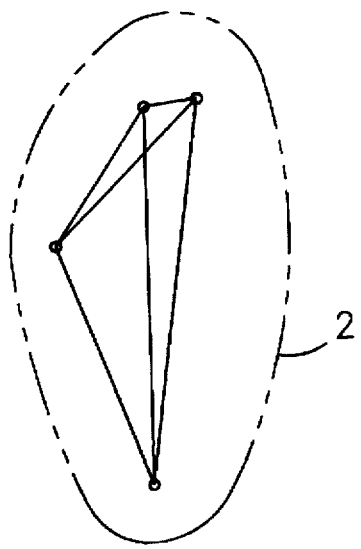
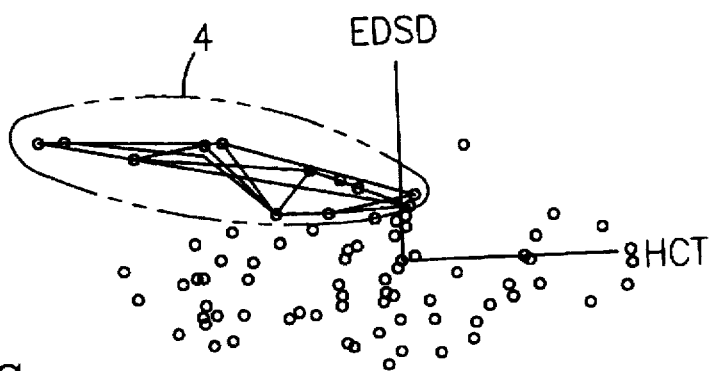
FIG. 4C

DETECTING SPECIFIC MEDICAL CONDITIONS FROM ERYTHROCYTE DENSITY DISTRUBITION IN A CENTRIFUGED ANTICOAGULATED WHOLE BLOOD SAMPLE

TECHNICAL FIELD

This invention relates to the detection of specific medical conditions from erythrocyte density distribution (EDD) measurements in a centrifuged blood sample. More particularly, this invention relates to the detection of specific medical conditions which are characterized by variations from norm in one or more of the following: skewness in the EDD curve; standard deviation of the EDD curve; mean density of the EDD curve; and the hematoorit (HCT) or hemoglobin (HGB) values of the blood sample. The term "skew" or "skewness" as used in connection with this invention relates to any deviations from Gaussian of the EDD curve, whether they be symmetrical or asymmetrical. Instead of measuring erythrocyte density directly, the hemoglobin concentration (HC) of individual erythrocytes can be measured by a cell counter, and skewness, standard deviation, and mean population HC can be derived from the individual HC measurements. The curves derived from the HC information should be identical to the curves derived from the EDD information.

BACKGROUND ART

U.S. Pat. No. 5,321,975 granted Jun. 21, 1994 to Robert A. Levine et al describes a procedure for measuring differential erythrocyte counts. The procedure involves the placement of a plurality of beads or discs of differing density or specific gravity in a blood sampling tube so that blood drawn into the tube will intermingle with the beads or discs. The blood sample is anticoagulated whole blood, and the beads or discs have specific gravities which are within the range of the specific gravity of the erythrocytes in the blood sample. The older erythrocytes in blood have a higher specific gravity than the younger erythrocytes due to a gradual loss of intracellular water from the cells as they age. Erythrocytes in healthy humans have an expected life of about one hundred twenty days. When the blood sample/bead/disc mixture is centrifuged, the erythrocytes in the blood sample will gravitate to the bottom of the sampling tube where they will form a packed erythrocyte layer, with the older cells being toward the bottom of the cell layer and the younger cells being toward the top of the cell layer. The beads or discs will settle into the packed erythrocyte layer at different levels therein so as to form spaced apart marker bands which are visible or detectable within the erythrocyte layer. The beads or discs will have respective specific gravities that are preferably 0.005 apart from each other. If the blood sample has experienced conventional erythrocyte production and loss during the preceding one hundred twenty days, the marker bands will be spaced apart from each other in the erythrocyte layer in a manner such that a plot of the percent of cells having a given density range results in a Gaussian curve. On the other hand, if there has been some anomaly in erythrocyte production or loss during the one hundred twenty day period, some of the marker bands will be closer to or further apart from each other than with a normal patient. In this manner, a histogram of erythrocyte production and/or loss can be derived as described in U.S. Pat. No. 5,321,975 granted Jun. 21, 1994 to R. A. Levine et al. When an abnormal histogram is noted, further tests can be conducted to try to discover the reason for the abnormality.

DISCLOSURE OF THE INVENTION

We have discovered that the centrifugation techniques described in the aforesaid patent to determine erythrocyte density distributions can also be used in conjunction with a conventional HCT test or HGB to detect abnormal medical conditions which are not limited to abnormal erythrocyte production or loss. A technique for centrifugally measuring HGB is described in U.S. Pat. No. 4,843,869 granted Jul. 4, 1989 to R. A. Levine et al, which patent is incorporated herein in its entirety. It is also possible to detect abnormal medical conditions by measuring HC in individual erythrocytes with an instrument sold by Technicon under the model name H-2. Since erythrocyte density is determined primarily by the concentration of hemoglobin within the cells, the HC determined in individual erythrocytes can be used as a surrogate for erythrocyte density. The H-2 instrument is also able to determine HCT in a blood sample being analyzed.

In healthy mammals, the erythrocyte density distribution (EDD) histogram produced by the aforesaid techniques will display Gaussian or near-Gaussian distributions which may be characterized by their mean, their standard deviation, and the lack of skewness of the EDD curve. Abnormalities observed in EDD mean, EDD standard deviation and/or EDD curve skewness may be indicative of abnormal erythrocyte-related medical conditions. These factors, when considered together with HCT readings, can be used to detect certain medical conditions which are distinguished by abnormal erythrocyte characteristics. These medical conditions include, but are not limited to: thalassemia minor; thalassemia intermedia; iron deficiency with anemia; iron deficiency without anemia; anemia of chronic illness; compensated hemolysis; and chronic or episodic bleeding, for example. Other erythrocyte-related medical conditions, such as sickle cell anemia, may also be identifiable by the procedure of this invention. The above anomalies in the aforesaid EDD curves which may be determinative of abnormal physical conditions also apply to like HC curves.

It is, therefore, an object of this invention to provide a method for analyzing an anticoagulated whole blood sample to determine the presence or absence of an abnormal medical condition which is distinguished by certain characteristics of an erythrocyte histogram of the blood sample derived either from observed erythrocyte density distribution, or from a plurality of observed individual erythrocyte HC readings.

It is a further object of this invention to provide a method of the character described wherein an erythrocyte density distribution or HC distribution curve is analyzed to detect variations from Gaussian or near-Gaussian distribution of the curve.

It is an additional object of this invention to provide a method of the character described wherein the blood sample is analyzed to measure its HCT in addition to its erythrocyte density distribution curve.

It is another object of this invention to provide a method of the character described wherein EDD standard deviation, mean EDD, and EDD curve skewness are measured to analyze the EDD curve.

These and other objects and advantages of the invention will become more readily apparent from the following detailed description of a preferred embodiment of the invention, when taken in conjunction with the accompanying drawings, in which:

BRIEF DESCRIPTION OF THE DRAWINGS

FIG. 1 is an EDD ogive plot for a blood sample taken from an individual who is not afflicted with the thalassemia syndrome;

FIG. 2 is an EDD ogive plot similar to FIG. 1, but taken from an individual who is afflicted with thalassemia minor;

FIGS. 4, 4a, 4b and 4c are different Y axis rotational views of a two dimensional projection of an X, Y, Z plot of the HCT readings; and the mean density values and standard deviations in EDD density of EDD histograms for a group of healthy individuals, a group of individuals with thalassemia minor, and a group of individuals with thalassemia intermedia.

BEST MODE FOR CARRYING OUT THE INVENTION

This invention has been shown to be useful in diagnosing the presence and type of thalassemia in an individual's genetic makeup. Genes for thalassemia are present in about 5% to about 15% of individuals of Mediterranean descent, and are also common in individuals of Asian and African descent. Depending on the genetics, the clinical and hematologic manifestations of thalassemia range from life-threatening, to minimal, to none. Iron overload and its complications are frequent in thalassemia. Thalassemias are a heterogeneous group of syndromes having in common the deficient regulation of the rate of synthesis of one or more of the polypeptide chains of the normal human hemoglobins.

Common types of thalassemia include: thalassemia minor; and thalassemia intermedia. Thalassemia minor refers to heterozygousity for a thalassemia gene. The anemia is mild with an average hemoglobin value which is lower than for normal individuals of the same age and gender, but which is not life threatening. Symptoms are typically absent. Thalassemia intermedia is a more severe form of the illness which is caused by multiple genetic factors. Individuals with thalassemia intermedia are able to maintain normal levels of hemoglobin without regular blood transfusions. The anemia associated with thalassemia intermedia is microcytic and hypochromic. Physical examination reveals skeletal changes and hepatosplenomegaly. Individuals afflicted with thalassemia intermedia generally survive to adulthood, but seldom into old age. Complications in adult life include pathologic fractures, cholelithiasis, and thoracic masses composed of hematopoietic tissue. The primary cause of premature death of such individuals is cardiac hemosiderosis. Testing for the presence of thalassemia, either minor or intermedia, is desirable since genetic counseling would be beneficial if either condition were identified.

The presence of thalassemia affects the overall density gradient of the erythrocyte pack in a centrifuged sample of an individual's anticoagulated whole blood. Thus generic thalassemia, and degrees thereof, can be detected and identified from an EDD histogram and HCT measurements taken from a centrifuged sample of an individual's anticoagulated whole blood. The drawings illustrate typical erythrocyte ogive curves which will be obtained from three different subject individual populations and graphs showing clustering of certain of the measured parameters for individuals with similar medical conditions. One of the individual populations is not afflicted with thalassemia; one is afflicted with thalassemia minor; and one is afflicted with thalassemia intermedia.

Figure 3:
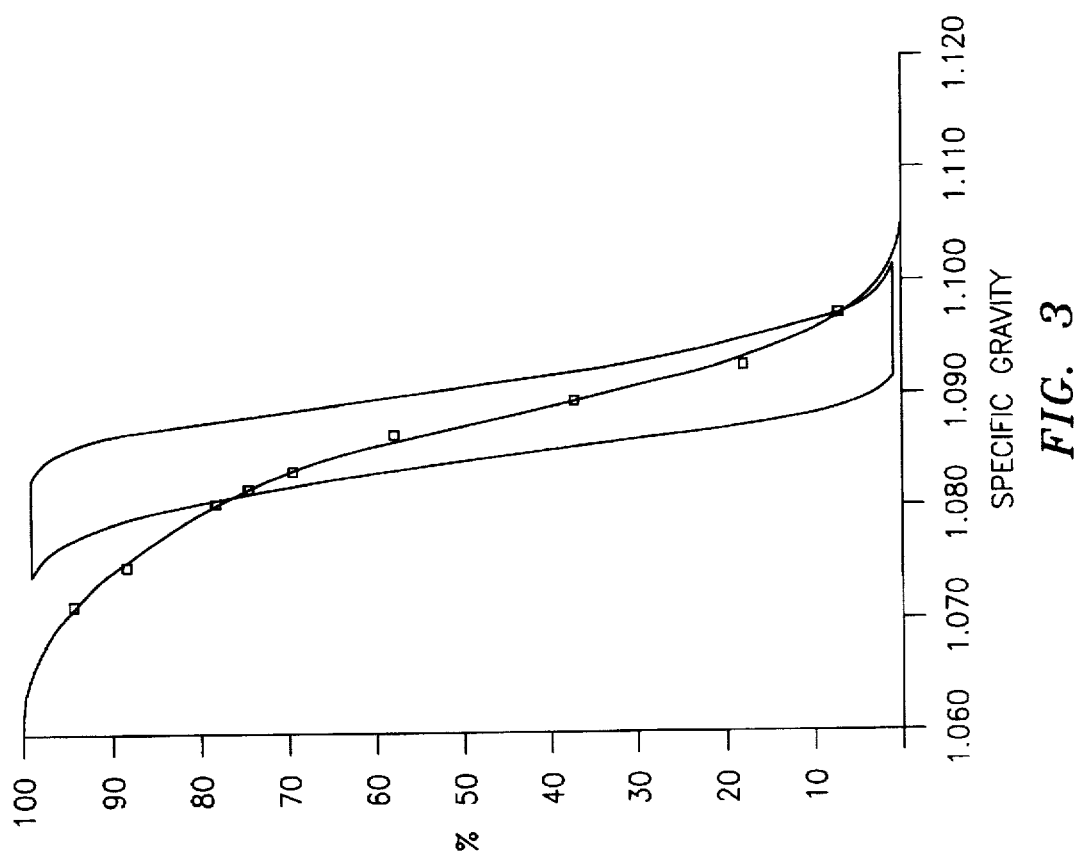
FIG. 3 is an EDD ogive plot similar to FIGS. 1 and 2 but taken from an individual who is afflicted with thalassemia intermedia.

FIGS. 1–3 are EDD ogive curves plotting the spatial distribution of known specific gravity inserts in the packed erythrocyte layer of a centrifuged sample of blood. These curves were obtained by centrifuging heparin anticoagulated whole blood samples in tubes which contain a plurality of disc-shaped inserts made from plastics, with each insert having a specific gravity which is different from the specific gravity of any of the other inserts, and with the specific gravity of each of the inserts being within the expected range of specific gravities for the erythrocytes in anticoagulated whole blood. The curve shown in FIG. 1 was obtained using twelve inserts; the curve shown in FIG. 2 was obtained using ten inserts; and the curve shown in FIG. 3 was obtained using twelve inserts. The lightest of the inserts had a specific gravity of 1.069 and the heaviest of the inserts had a specific gravity of 1.1090. The intermediate inserts had specific gravities that differed from one another by known intervals. The inserts were placed in the blood sampling tube prior to drawing the blood sample in the tube with the heaviest of the inserts toward the bottom of the tube and the lightest toward the top of the tube. The curves in each of FIGS. 1–3 show the percent of erythrocytes below a certain specific gravity or density on the "Y" axis, and show the specific gravity or density range for the erythrocytes on the "X" axis.

In each of FIGS. 1–3, the shaded bands indicate the expected EDD ogive curve for an individual who is not suffering from thalassemia, an individual who can be characterized in this instance as a "normal" individual. Any individual with an EDD histogram plot that remains completely in the shaded area would not be thought to possess a thalassemia trait. FIG. 1 shows such a "normal" EDD curve. The EDD ogive curve shown in FIG. 2 is from an individual possessing the thalassemia minor trait. It will be noted that the mean density of the erythrocytes plotted in FIG. 2 is somewhat lower than the mean density of the erythrocytes plotted in FIG. 1; and that the standard deviation of the EDD curve in FIG. 2 is somewhat higher than the standard deviation of the EDD curve in FIG. 1.

FIG. 3 shows an EDD ogive curve plot of the erythrocytes of an individual having the thalassemia intermedia trait. It will be noted that while the mean density of the erythrocyte curve shown in FIG. 3 is essentially the same as the mean density of the erythrocyte curve shown in FIG. 1, the standard deviation of the EDD curve in FIG. 3 is much greater than the standard deviation of the EDD curve in FIG. 1. Additionally, the skewness of the EDD curve in FIG. 3 is much greater than the skewness of the EDD curve in FIG. 1. FIGS. 1–3 are indicative of differences between various characteristics of the EDD ogive curves of "normal" individuals; individuals with thalassemia minor trait; and individuals with thalassemia intermedia trait.

Figure 4:
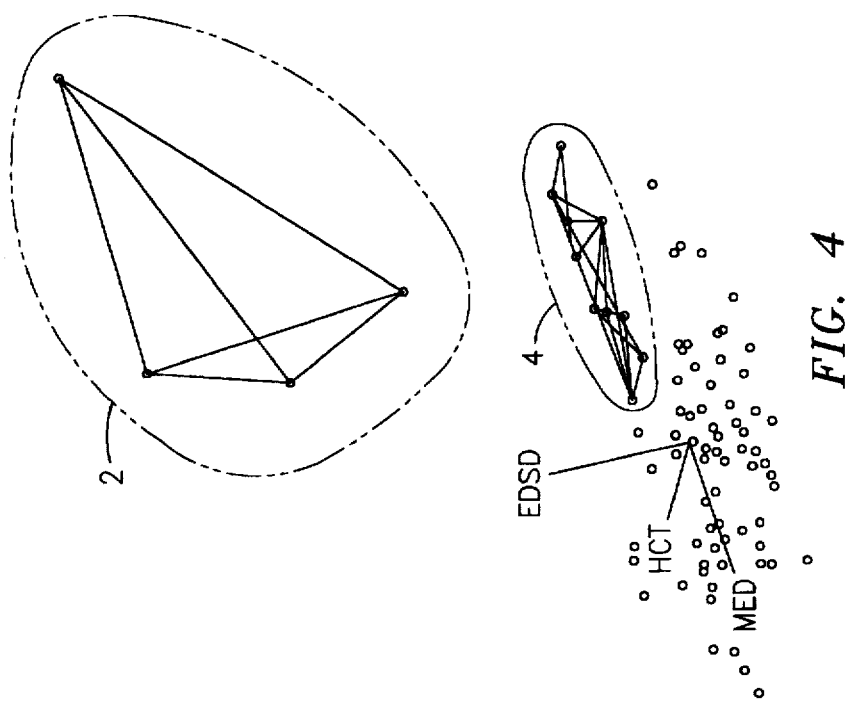

As noted above, HCT values can also be used to assist in the diagnoses of thalassemia minor and intermedia traits in conjunction with the EDD curves. It will be appreciated that each of the data points shown in FIGS. 4, 4a), 4b), 4c) and FIG. 5 represents a different individual's erythrocyte value.

FIGS. 4a), b), and c) are different rotational views of a two dimensional projection of a three dimensional plot of HCT; erythrocyte density standard deviation (EDSD); and mean erythrocyte density (MED) of EDD histograms taken from a population that includes "normal" individuals; individuals with the thalassemia minor trait; and individuals with the thalassemia intermedia trait. It will be noted that data from the various individuals in the population tends to form clusters when the data is analyzed in three dimensions. The various clusters are characterized by deviations in certain of the EDD parameters being measured. It will be noted from FIGS. 4a), b) and c) that one cluster 2 of data points, all of which are interconnected by lines for clarity sake, and contained within broken line circles demonstrates a large deviation in EDSD from the remaining data points. This cluster 2 identifies a group of individuals who have the thalassemia intermedia trait. It will be noted that this cluster 2 is also characterized by markedly decreased HCT values as compared to the remainder of the individuals. It will also be noted from FIGS. 4a), b) and c) that another identifiable cluster 4 of individual data points, which are also interconnected by lines for the sake of clarity, and are contained within broken line circles, and demonstrates a decrease in MED from the normal population. This cluster 4 identifies a group of individuals who have the thalassemia minor trait.

Figure 5:
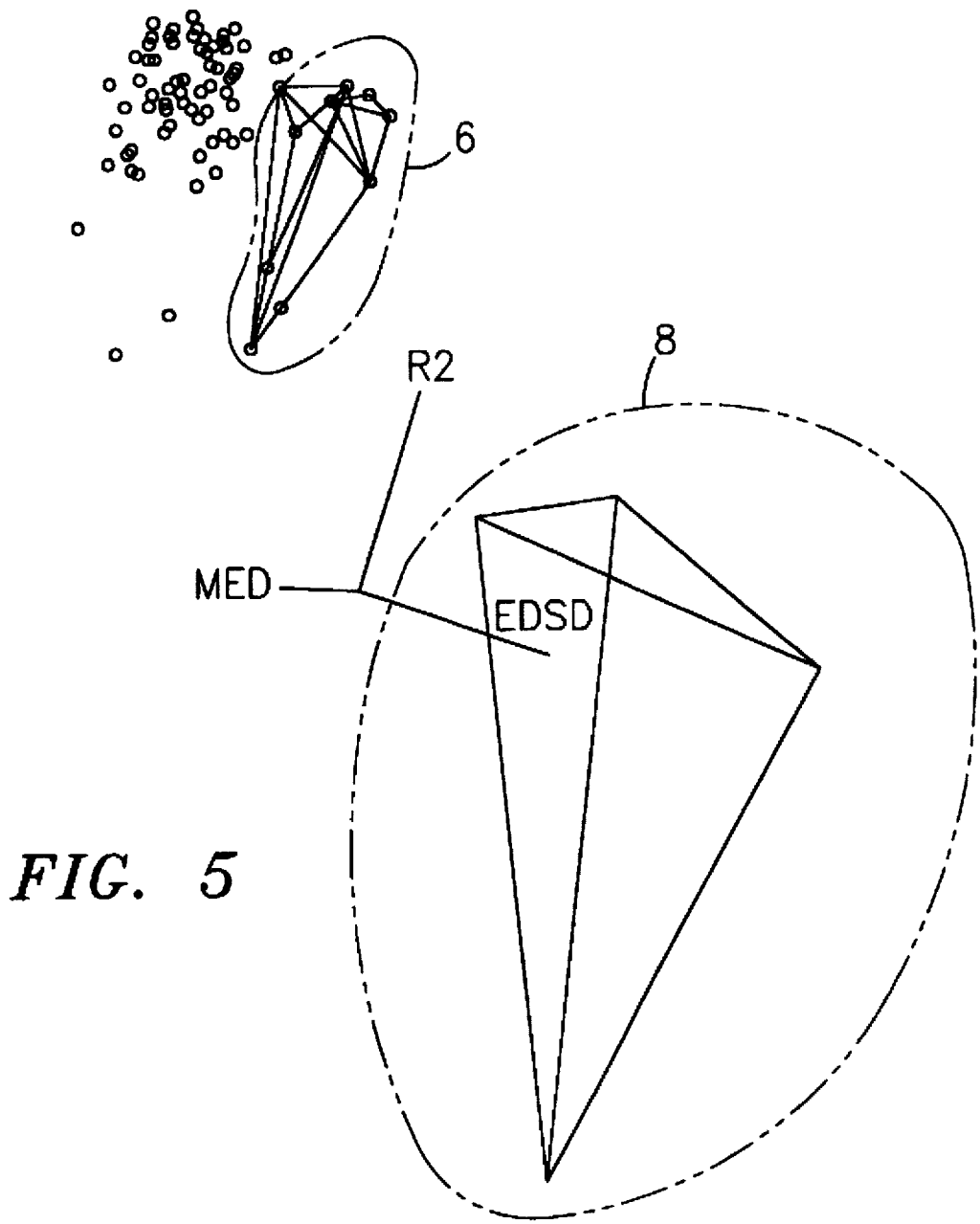
FIG. 5 is a two dimensional projection of an X, Y, Z plot but showing mean density values, standard deviations in EDD density, and skewness $R^2$ of the EDD histograms for similar groups of individuals.

FIG. 5 is a two dimensional projection of a three dimensional plot of EDD histogram skew ($R^2$); erythrocyte density standard deviation (EDSD); and mean erythrocyte density (MED) of EDD histograms taken from a population that includes "normal" individuals; individuals with the thalassemia minor trait; and individuals with the thalassemia intermedia trait. It will be noted that a cluster 6 of individual interconnected data points contained within a broken line circle in FIG. 5 demonstrates a marked deviation in $R^2$ from the remainder of the individual data points. The individual data points contained within the cluster 6 are taken from individuals who have the thalassemia intermedia trait. It will also be noted that a second cluster 8 of individual interconnected data points contained within a broken line circle in FIG. 5 demonstrates a marked deviation in $R^2$ from the remainder of the individual data points. The individual data points contained within the cluster 8 are taken from individuals who have the thalassemia minor trait.

The aforesaid demonstrates the utility of this invention for the diagnosis of certain genetic thalassemia traits which produce certain identifiable and detectable anomalies in an ogive curve derived from an EDD histogram of a blood sample from an individual possessing one of the traits. The invention can also be used to detect other medical conditions which are characterized by two or more of the aforesaid deviations from the norm in HCT; EDD MED; EDD EDSD; and/or EDD $R^2$. As noted first above, the invention can be used to detect iron deficiency without anemia in an individual; iron deficiency anemia in an individual; compensated hemolysis or bleeding in an individual; chronic or episodic bleeding in an individual; and may also be useful in detecting other medical conditions which are distinguished by variations from the norm in erythrocyte parameters.

As noted above, instead of measuring the EDD of a centrifuged erythrocyte layer, one can measure the HC of a plurality of individual erythrocytes and HCT in a cell counter of the H-2 type sold by Technicon Corp.. The individual cell readings can then be analyzed to determine the mean HC; the standard deviation of the HC values; and the skewness of the HC values. The results obtained by these calculations can be used in lieu of the EDD-derived determinations.

It is noted that erythrocyte parameters taken from a "normal" male are useful for providing a baseline from which to detect erythrocyte deviations for the HCT and EDD parameters. If one uses "normal" males as a baseline, it will first be noted that "normal" females will exhibit a slightly less than baseline MED; the same as baseline EDSD; a slightly less than baseline HCT; and the same as baseline $R^2$.

The following is a listing of erythrocyte deviations which have been observed when certain of the above conditions are present in an individual, and which will be detected by use of the procedure of this invention.

1) Iron deficiency without anemia: substantially lower than baseline MED; same as baseline EDSD; baseline to slightly lower than baseline HCT; and baseline to slightly greater than baseline $R^2$;

2) Iron deficiency anemia: substantially lower than baseline MED; substantially higher than baseline EDSD; substantially lower than baseline HCT; and baseline to slightly higher than baseline $R^2$;

3) Compensated hemolysis or bleeding: baseline to slightly lower than baseline MED; substantially higher than baseline EDSD; baseline to slightly lower than baseline HCT; and substantially higher than baseline $R^2$; and 4) chronic or episodic bleeding: baseline to slightly lower than baseline MED; substantially higher than baseline EDSD; baseline to slightly lower than baseline HCT; and substantially higher than baseline $R^2$.

Other medical conditions may be studied to ascertain the applicability of the invention to the diagnosis thereof. It will be appreciated that when the procedure of this invention detects any evidence of an erythrocyte-related abnormality in a patient's blood sample, further tests should be conducted in order to confirm or rule out the presence of any suspected medical condition.

It will be readily appreciated that the procedure of this invention may be used to identify certain abnormalities in mammals which abnormalities are characterized by certain erythrocyte parameters. The EDD procedure can be performed in a short period of time, does not require a high degree of technical training, and results can be obtained with an automated instrument of the general type sold by Becton Dickinson and Company under the trademark "Autoreader". The paraphernalia needed to run the test are inexpensive and compact. It will also be appreciated that the density markers can take the form of discs, beads, or have any other suitable geometry.

Since many changes and variations of the disclosed embodiment of the invention may be made without departing from the inventive concept, it is not intended to limit the invention otherwise than as required by the appended claims.

What is claimed is:

1. A method for detecting abnormal mammalian physiologic conditions which are characterized by deviations from norm of certain erythrocyte parameters in a donor blood sample, said method comprising the steps of:

a) providing a sample tube containing a sample of mammalian anticoagulated whole blood from a blood donor and a plurality of artificial density markers which are operable to form gravimetrically separated discernible reference lines in the blood sample, each reference line forming an upper boundary for one erythrocyte band and a lower boundary for a next adjacent erythrocyte band, the density of each density marker being within an expected range of densities of erythrocytes;

b) centrifuging the sample tube so as to gravimetrically separate the erythrocytes into an erythrocyte column which is separate from the remaining components of the blood sample, and so as to embed the density markers in the erythrocyte column whereby erythrocyte subsets in an erythrocyte density distribution (EDD) gradient are demarcated by the reference lines created by the embedded density markers in the erythrocyte column;

c) measuring and recording distances between adjacent density marker reference lines in the erythrocyte column to provide a plurality of EDD values;

d) defining an EDD curve from said EDD values;

e) determining the erythrocyte density standard deviation (EDSD), mean erythrocyte density (MED), and curve skewness ($R^2$) in said defined EDD curve; and f) comparing any noted differences in two or more of the determined EDSD, MED and $R^2$ with empirical EDSD, MED and $R^2$ EDD curve data which have been derived from physiologically abnormal mammalian populations in order to determine whether any such differences are indicative of an abnormal physiologic condition in the blood donor.

2. A method for detecting abnormal mammalian physiologic conditions which are characterized by deviations from norm of certain erythrocyte parameters in a donor blood sample, said method comprising the steps of:

a) providing a sample tube containing a sample of mammalian anticoagulated whole blood from a blood donor and a plurality of artificial density markers which are operable to form discernible bands in the blood sample, each density marker in each band having a different density from density markers in any other band, and the density of each density marker being within an expected range of densities of erythrocytes;

b) centrifuging the sample tube so as to gravimetrically separate the erythrocytes into an erythrocyte column which is separate from the remaining components of the blood sample, and so as to embed the density markers in the erythrocyte column whereby erythrocyte subsets in an erythrocyte density distribution (EDD) gradient are demarcated by density markers which are embedded in the erythrocyte column;

c) measuring and recording distances between adjacent density markers in the erythrocyte column to provide a plurality of EDD values;

d) determining an EDD curve from said EDD values;

e) measuring and recording a hematocrit (HCT) value from said erythrocyte column to provide an HCT value for the centrifuged blood sample;

f) defining the erythrocyte density standard deviation (EDSD), mean erythrocyte density (MED), and curve skewness ($R^2$) in said determined EDD curve;

g) comparing any noted differences in one or more of EDSD, MED, $R^2$ and HCT with empirical EDSD, MED and $R^2$ EDD curve data, and with HCT data, which have been derived from physiologically abnormal mammalian populations to determine whether any observed differences, or any combination thereof, are indicative of an abnormal physiologic condition in the blood donor.

3. A method for detecting abnormal mammalian physiologic conditions which are characterized by deviations from normal erythrocyte density standard deviation (EDSD) in a donor sample of blood, said method comprising the steps of:

a) providing a sample tube containing a sample of mammalian anticoagulated whole blood from a blood donor and a plurality of artificial density markers which are operable to form discernible bands in the blood sample, each density marker in each band having a different density from density markers in any other band, and the density of each density marker being within an expected range of densities of erythrocytes;

b) centrifuging the sample tube so as to gravimetrically separate the erythrocytes into an erythrocyte column which is separate from the remaining components of the blood sample, and so as to embed the density markers in the erythrocyte column whereby erythrocyte subsets in an erythrocyte density distribution (EDD) gradient are demarcated by density markers embedded in the erythrocyte column;

c) measuring and recording distances between adjacent density markers in the erythrocyte column to provide a plurality of EDD values;

d) determining a donor EDD curve from said EDD values;

e) defining the erythrocyte density standard deviation (EDSD) in said donor EDD curve; and f) comparing any noted differences in said defined EDSD with empirical EDSD curve data which have been derived from physiologically abnormal mammalian populations to determine whether any such differences are indicative of an abnormal physiologic condition in the blood donor.

4. A method for detecting abnormal mammalian physiologic conditions which are characterized by deviations from norm of mean erythrocyte density (MED) in a sample of blood from a blood donor, said method comprising the steps of:

a) providing a sample tube containing a sample of donor mammalian anticoagulated whole blood and a plurality of artificial density markers which are operable to form discernible bands in the blood sample, each density marker in each band having a different density from density markers in any other band, and the density of each density marker being within an expected range of densities of donor erythrocytes;

b) centrifuging the sample tube so as to gravimetrically separate the donor erythrocytes into a donor erythrocyte column which is separate from the remaining components of the donor blood sample, and so as to embed the density markers in the donor erythrocyte column whereby erythrocyte subsets in a donor erythrocyte density distribution (EDD) gradient are demarcated by density markers embedded in the erythrocyte column;

c) measuring and recording distances between adjacent density markers in the erythrocyte column to provide a plurality of donor EDD values;

d) determining a donor EDD curve from said donor EDD values;

e) determining the MED in said donor EDD curve; and f) comparing any noted differences in donor MED with empirical abnormal MED curve data which have been derived from physiologically abnormal donor populations to determine whether any such noted differences are indicative of an abnormal physiologic condition in the blood donor.

5. A method for detecting mammalian physiologic conditions which are characterized by deviations from norm of curve skewness ($R^2$) of an erythrocyte density distribution (EDD) curve in a donor blood sample, said method comprising the steps of:

a) providing a sample tube containing a sample of mammalian anticoagulated whole blood from a blood donor and a plurality of artificial density markers which are operable to form discernible bands in the blood sample, each density marker in each band having a different density from density markers in any other band, and the density of each density marker being within an expected range of densities of erythrocytes;

b) centrifuging the sample tube so as to gravimetrically separate the erythrocytes into an erythrocyte column which is separate from the remaining components of the blood sample, and so as to embed the density markers in the erythrocyte column whereby erythrocyte subsets in an EDD gradient are demarcated by density markers embedded in the erythrocyte column;

c) measuring and recording distances between adjacent density markers in the erythrocyte column to provide a plurality of EDD values;

d) determining a donor EDD curve from said donor EDD values;

e) defining the $R^2$ in said donor EDD curve; and f) comparing any noted differences in $R^2$ with empirical $R^2$ EDD curve data which have been derived from physiologically abnormal mammalian populations in order to determine whether any such differences are indicative of an abnormal physiologic condition in the blood donor.

* * * * *